United States Patent
Su et al.

(10) Patent No.: US 7,148,057 B2
(45) Date of Patent: Dec. 12, 2006

(54) ARRAY BIOCHIP WORKSTATION

(75) Inventors: Yo-Hsin Su, Kaohsiung Hsien (TW);
Hsi-Lien Lu, Kaohsiung (TW);
Hsun-Min Lung, Fengshan (TW);
Chung-Ho Tung, Fengshan (TW);
Ta-Chang Liu, Kaohsiung (TW);
Chih-Kung Lee, Taipei (TW); Su-Ming Hsu, Kaohsiung (TW); Shiming Lin,
Taipei (TW); Long-Sun Huang, Taipei
(TW); Chii-Wann Lin, Taipei (TW)

(73) Assignee: Gongin Precision Industries, Co., Ltd,
Kaohsiung (TW)

( * ) Notice: Subject to any disclaimer, the term of this patent is extended or adjusted under 35 U.S.C. 154(b) by 756 days.

(21) Appl. No.: 10/216,911

(22) Filed: Aug. 13, 2002

(65) Prior Publication Data
US 2004/0033590 A1 Feb. 19, 2004

(51) Int. Cl.
*C12M 1/34* (2006.01)
(52) U.S. Cl. .................. 435/287.2; 435/287.3; 435/288.4; 435/288.7; 422/63; 422/130

(58) Field of Classification Search ............. 435/287.2, 435/287.3, 288.4, 288.5, 293.1; 422/100, 422/102, 52, 63, 65, 130; 366/118
See application file for complete search history.

(56) References Cited

U.S. PATENT DOCUMENTS

| | | | |
|---|---|---|---|
| 3,780,992 A | * | 12/1973 | Nishi et al. ................. 366/114 |
| 6,238,910 B1 | * | 5/2001 | Custance et al. ......... 435/287.2 |
| 2004/0029258 A1 | * | 2/2004 | Heaney et al. ........... 435/287.2 |

* cited by examiner

*Primary Examiner*—William H. Beisner
(74) *Attorney, Agent, or Firm*—Birch, Stewart, Kolasch & Birch, LLP (57) ABSTRACT

A microarray biochip workstation allowing positioning of chips, immobilization of molecules, mixing of sample solution, molecular interactions and washing and processing qualitative and quantitative analyses consists of a positioning device for holding a biochip, a mixing device for acting on the sample solution applied on the biochip, a pumping device for removing the sample solution from the biochip surface that does not react, and a reading device for detecting reaction results of the biochip. The workstation thus constructed provides an integrated and effective work interface.

9 Claims, 11 Drawing Sheets

ARRAY BIOCHIP WORKSTATION

FIELD OF THE INVENTION

The present invention relates to an array biochip workstation and particularly to a workstation that allows positioning of chips, immobilization of molecules, mixing of sample solution, molecular interactions and washing and processes qualitative and quantitative analyses of testing.

BACKGROUND OF THE INVENTION

Biochips are high-tech biological elements designed based on principles of molecular biology, protein chemistry, analytic chemistry and optoelectronics and bioformation, and are manufactured by employing Micro Electro Mechanical System, precision manufacturing and other automatic processes. Their applications cover life science basic research, biomedical diagnosis, new drug discovery, and food safety, and the likes.

The techniques being used include immobilizing biological probes (mainly originating from nucleic acid, protein, carbonhydrate, cells, tissues or the likes) on a substrate, then biological sample solution (such as blood, urine, body fluid, or saliva) containing a target to be tested is mixed on the chip. As the target and the corresponding biological probes have specificity, molecular interactions such as binding reaction or enzyme-catalytic reaction may occur, and resulting in alteration of signals (including optical, piezoelectric, electrochemical, energy signals), or labelling methods such as colormetric, fluorimetric, chemiluminescent or radiative detection may be employed to do image analyses and quantitate optical or radiative intensity of the probe-target complexes to obtain the information of the tested sample.

Many conventional methods for processing biochips such as immobilizing biological probes, mixing sample solution, molecular interaction, and washing and separation are done manually without continuity. They are mostly time-consuming and tedious. The steps used generally include immobilizing biological probes, applying biological sample solution, holding biochips still for molecular interactions for a selected time period, then washing manually and consecutively for a number of times, or utilizing a shaking device to perform mixing operation and manually replacing buffer solution a number of times for washing and separation. The discontinuous operating steps and various devices being used tend to incur problems such as (1) manual control tends to incur time variances, (2) washing by shaking does not have consistent force and tends to damage binding, (3) array spot on the array biochip cannot be anchored and separated properly and may result in solution pollution with each other, (4) washing and removing of solution are not done thoroughly or completely and tend to have residual fluid remained, and (5) scanning is not done timely to detect reaction signals on the array biochip. As a result, errors could incur in signal detection or image analysis.

SUMMARY OF THE INVENTION

Therefore the primary object of the invention is to resolve aforesaid disadvantages. The invention provides a complete workstation to reduce the errors mentioned above, and to combine functions of positioning for the array spots of the biochip, mixing, interaction, washing and separation, and scanning and reading in the same device body to facilitate integrated operation and utilization for users.

In order to achieve the foregoing objects, the array biochip workstation of the invention consists of a positioning device for holding a biochip, a mixing device for acting on sample solution applied on the biochip, a pumping device for removing the sample solution from the biochip surface that do not react, and a reading device for detecting reaction results of the biochip. The array biochip that has biological probes immobilized thereon is placed in the positioning device, or the chip is placed in the positioning device and biological probes are immobilized thereon, then add sample solution, then dispose the mixing device over corresponding to array spots on the chip to do mixing, then wash and remove the sample solution that does not react through the pumping device, thereafter employ the reading device to process image analysis and comparison of the reaction results of array spots on the array biochip. The biochip workstation of the invention thus constructed can provide complete operations and reduce experimental errors.

The foregoing, as well as additional objects, features and advantages of the invention will be more readily apparent from the following detailed description, which proceeds with reference to the accompanying drawings.

BRIEF DESCRIPTION OF THE DRAWINGS

FIGS. 4-A, 4-B and 4-C are schematic views of the invention in various operating conditions.
FIGS. 5-A, 5-B and 5-C are other schematic views of the invention in various operating conditions.
FIGS. 6-A and 6-B are schematic views of another embodiment of the invention.

DESCRIPTION OF THE PREFERRED EMBODIMENTS

Figure 1:
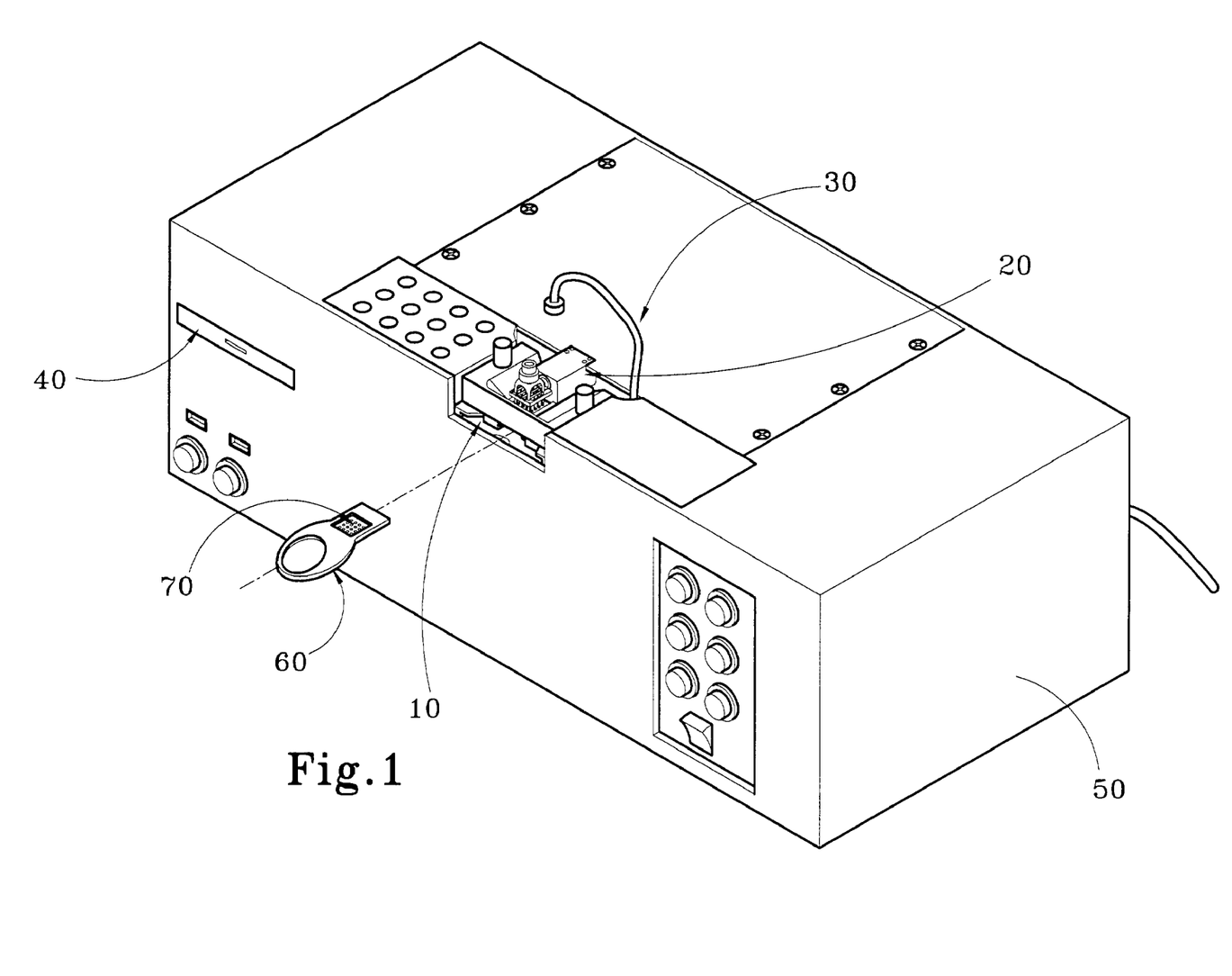
FIG. 1 is a perspective view of the invention.
Figure 2:
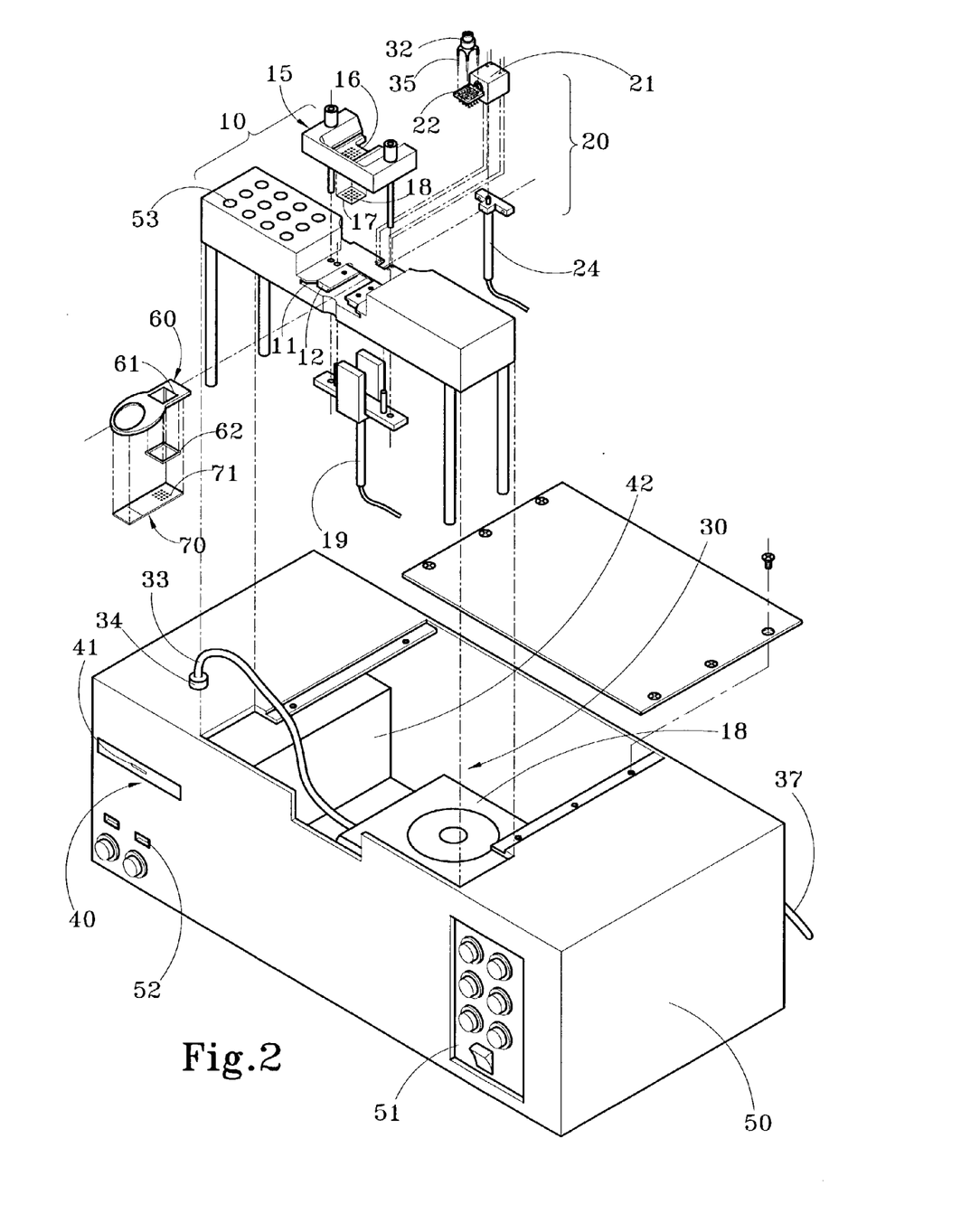
FIG. 2 is an exploded view of the invention.
Figure 3:
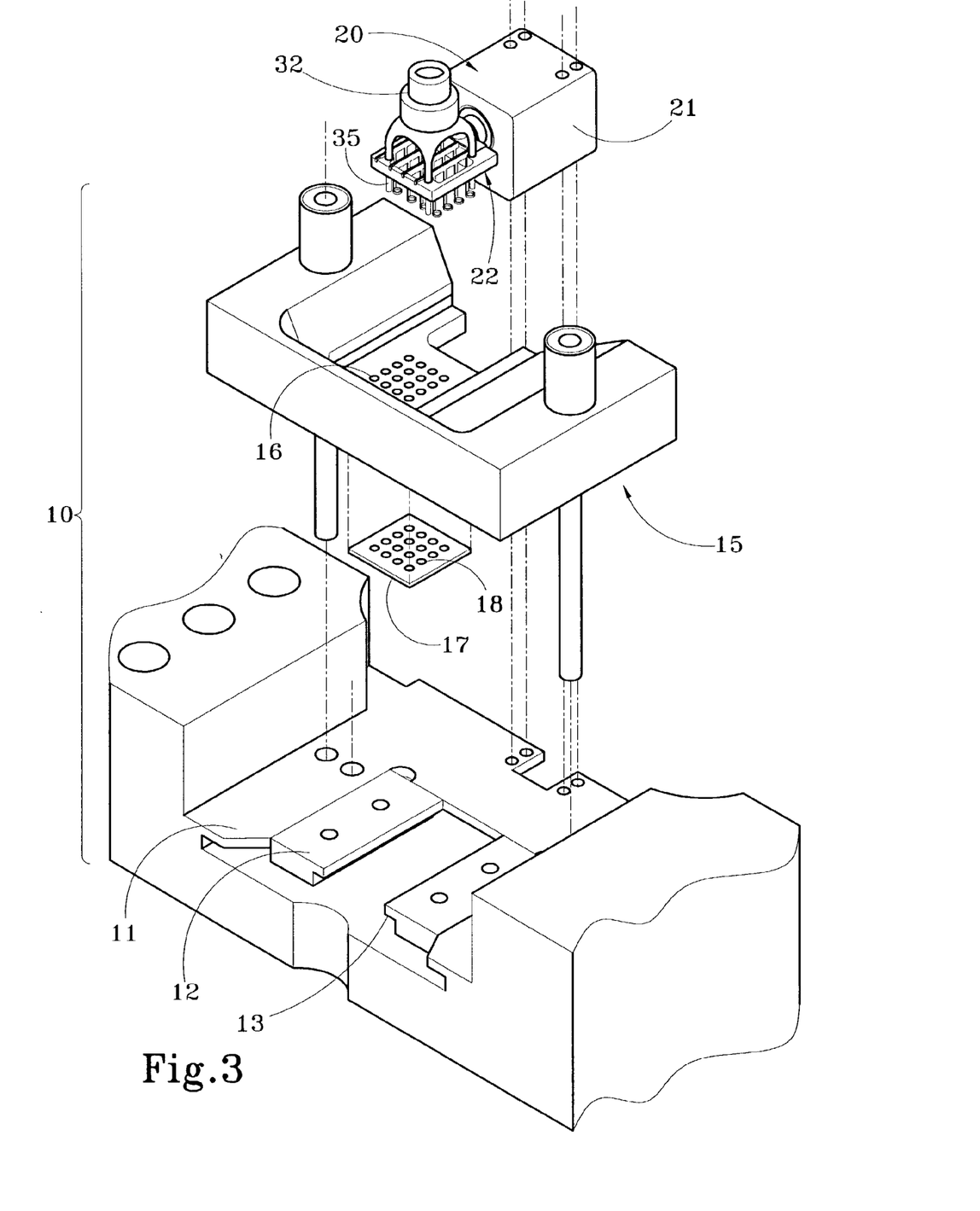
FIG. 3 is a fragmentary exploded view of the invention.

Referring to FIGS. 1, 2 and 3, the array biochip workstation of the invention aims at holding a biochip 70, and allowing biological probes 72 formed on array spots 71 of the biochip 70 to interact with sample solution 80, and processing qualitative and quantitative testing analyses. The workstation consists of a positioning device 10 for holding the biochip 70, a mixing device 20 for acting on sample solution 80 applied on the biochip 70, a drawing device 30 for removing the sample solution 80 on the biochip 70 that does not react, and a reading device 40 for detecting reaction results of the biochip 70. The biochip 70 that has biological probes 72 formed thereon is placed in the positioning device 10, or the biochip 70 is placed in the positioning device 10, then biological probes 72 are immobilized thereon, then sample solution 80 is added. The mixing device 20, through a separation unit 15, is used to process mixing on the corresponding array spots 71 of the biochip 70. Then the drawing device 30 is employed to remove the sample solution 80 that does not react from the biochip 70 surface. Then a drying process is performed. And the reading device 40 is used to do image analysis and comparison of reaction results for the biochip 70.

The positioning device 10 includes a guiding trough 11 for anchoring the biochip 70. The separation unit 15 is located on the guiding trough 11 for separating the array spots 71 of the biochip 70. The guiding trough 11 has two sides forming respectively an anchoring member 12 with a compressing section 13. The anchoring member 12 is harnessed by an elastic element 14. The biochip 70 may be held in a chip cartridge 60 which has two sides may be slipped in and clamped by the compressing section 13. The chip cartridge 60 has a test opening 61 whose periphery is coupled with a seeping guard 62 which may be compressed on the chip to form a common solution mixing zone for all array spots to prevent the sample solution 80 from flowing out.

In addition, the separation unit 15 has a bottom section attaching to a first displacement mechanism 19 which may drive the separation unit 15 moving in parallel and up or down. The separation unit 15 further has a plurality of separation holes 16 corresponding to array spots 71 of the biochip 70. The bottom section of the separation unit 15 further attaches to an anti-permeation pad 17 which has apertures 18 corresponding to the separation holes 16. When the separation unit 15 is moved downwards, the anti-permeation pad 17 compresses the biochip 70 with the apertures 18 matching respectively the array spots 71 to form reaction zones. The anti-permeation pad 17 is made from a pliable material such as rubber.

The mixing device 20 is located on the positioning device 10 and includes a mixing unit 22 passing through the separation unit 15 and corresponding to the array spots 71 for mixing the sample solution 80, and a oscillation unit 21 which has piezoelectric ceramic material to generate oscillation to actuate the mixing unit 22, thereby the biological probes 72 on the biochip 70 may be effectively enhanced to react with the sample solution 80. Moreover, the mixing device 20 has a bottom end attaching to a second displacement mechanism 24 for moving the mixing device 20 downwards to perform mixing operation.

The drawing device 30 includes a power unit 31 and a suction unit 32 fastening to the power unit 31 and being adjacent to the biochip 70. The power unit 31 has at least one suction pipe 33 and one discharge pipe 37 extending therefrom. The suction pipe 33 has a free end connecting to a connection head 34 of the suction unit 32. The suction unit 32 further has a suction needle 35 adjacent to the biochip 70. The suction needle 35 has a head end 36 which forms an obtuse truncated angle. The head end 36 is spaced from the array spots 71 of the biochip 70 for a selected interval to prevent reaction results from damaging when drawing operation is performed. The mixing unit 22 has at least one anchoring hole 23 to receive the suction needle 35.

The reading device 40 is for processing qualitative and quantitative scanning analyses for the array spots 71 on the biochip 70 that have gone through interaction, washing and drawing operations. It has an inlet 41 to receive the biochip 70. The reading device 40 may be a optical transmittant or reflective scanner 42 depending on the nature of the substrate and film property of the biochip 70.

In addition, the positioning device 10, the mixing device 20, the drawing device 30 and the reading device 40 are mounted on a device body 50. The device body 50 has at least one control panel 51 located on a surface thereof for controlling all other devices and at least one connection slot 52 for linking to a computer or other operation systems to process control and data analysis. The connection slot 52 may be a parallel transmission port or a series transmission port such as RS-232 or USB interface. Moreover, the device body 50 has at least one housing cavity 53 corresponding to two sides of the positioning device 10 for housing a container for holding reagents and the sample solution 80.

Figure 4A:
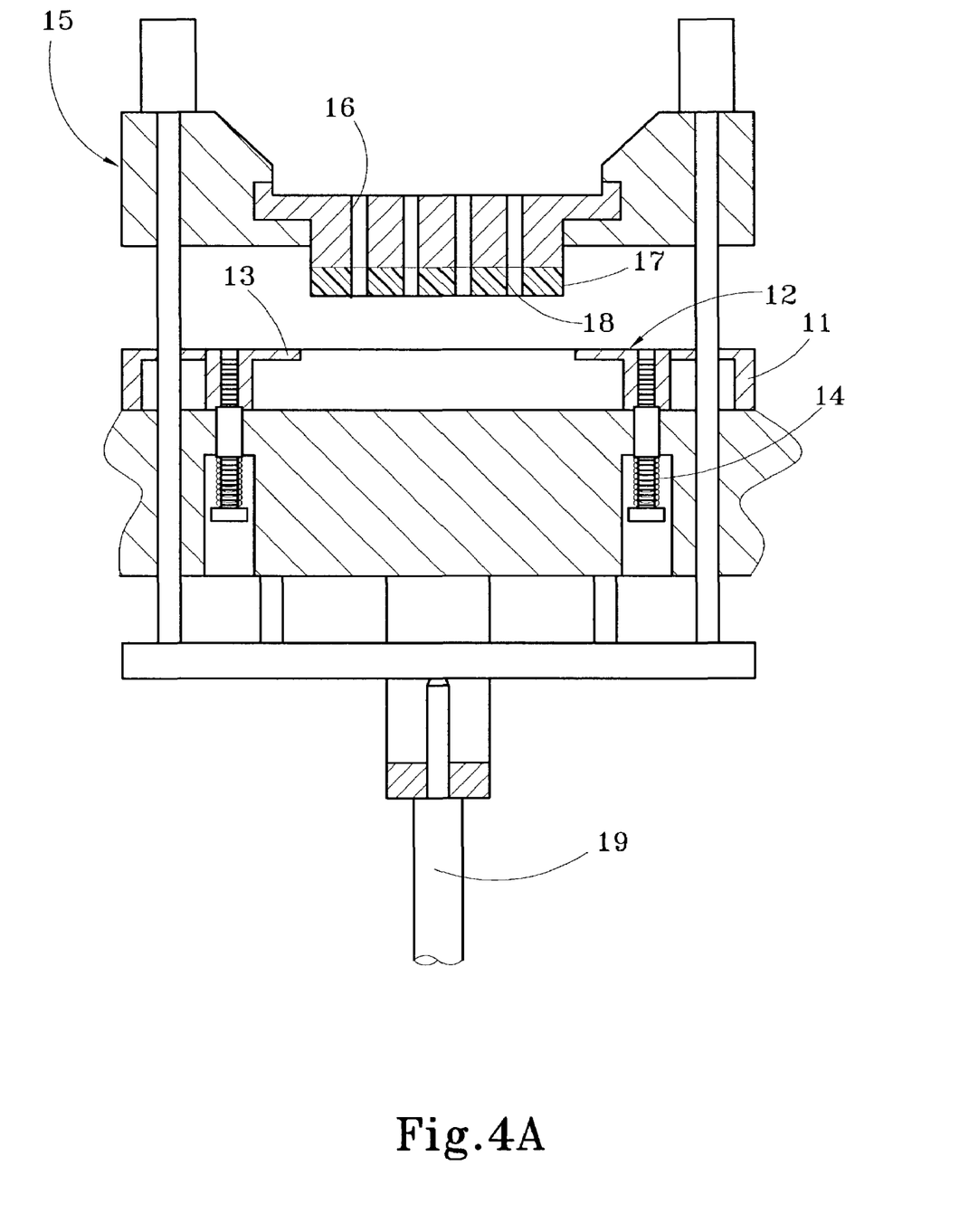
Figure 4B:
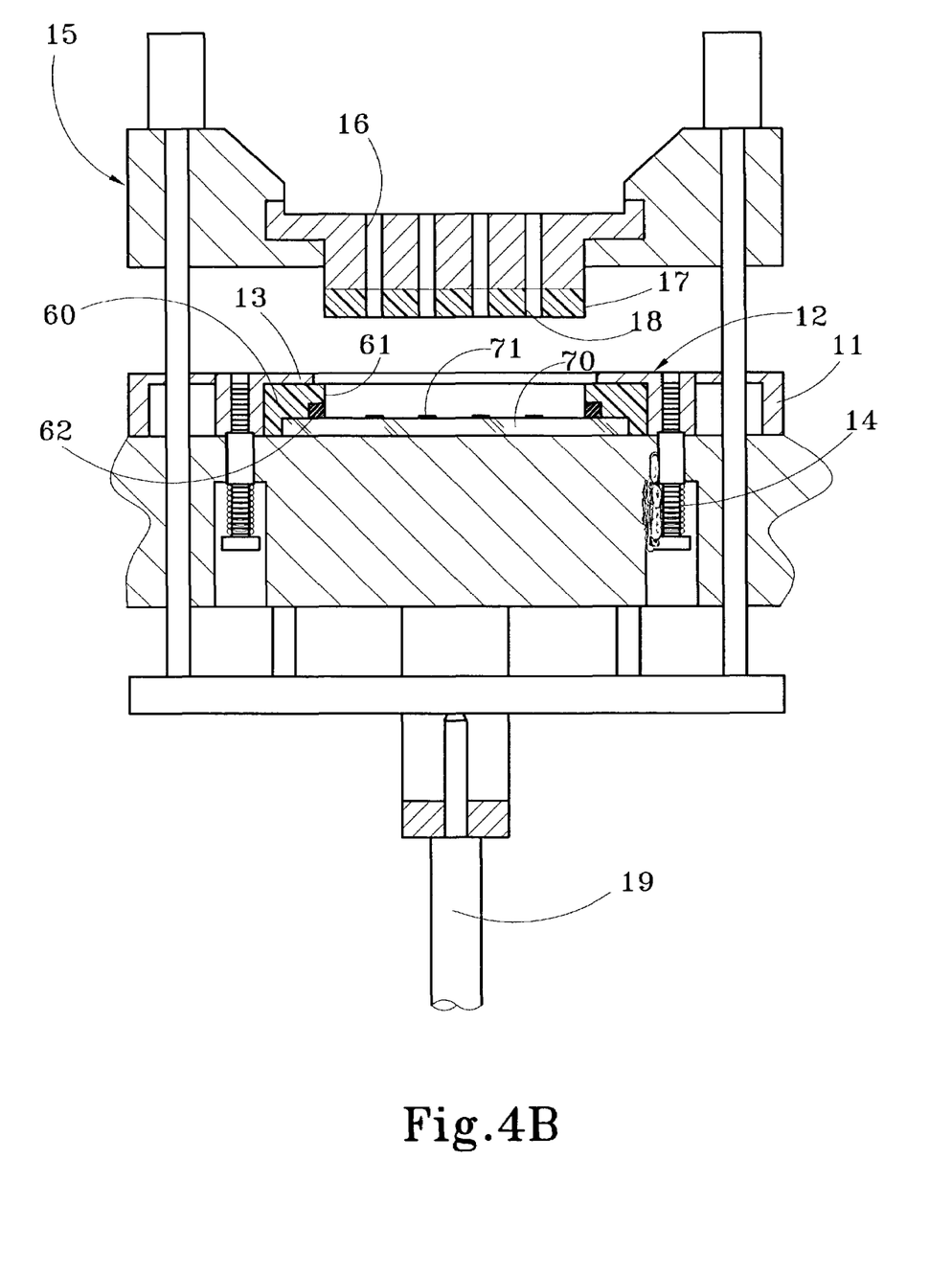
Figure 4C:
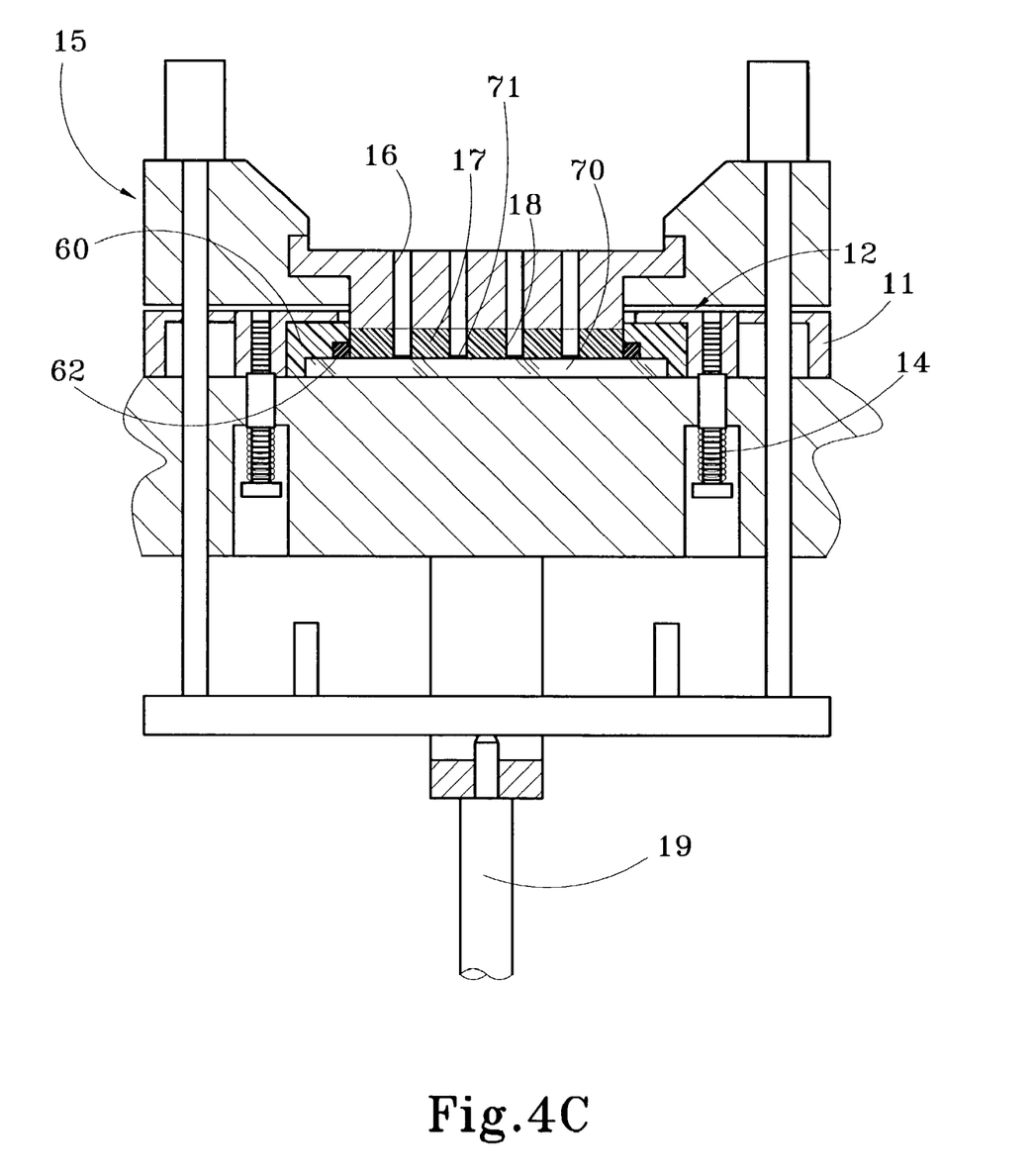
Figure 5A:
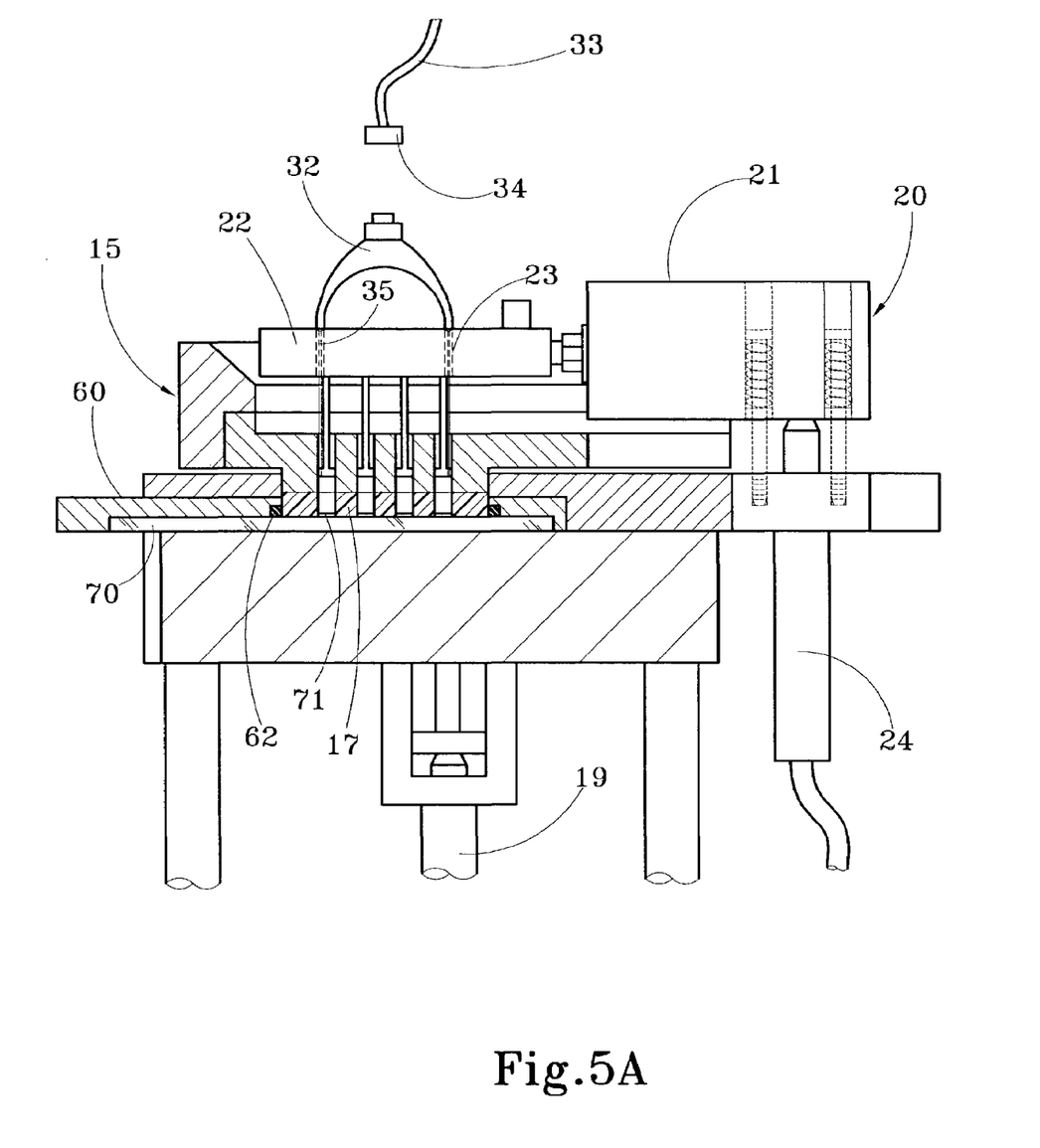
Figure 5B:
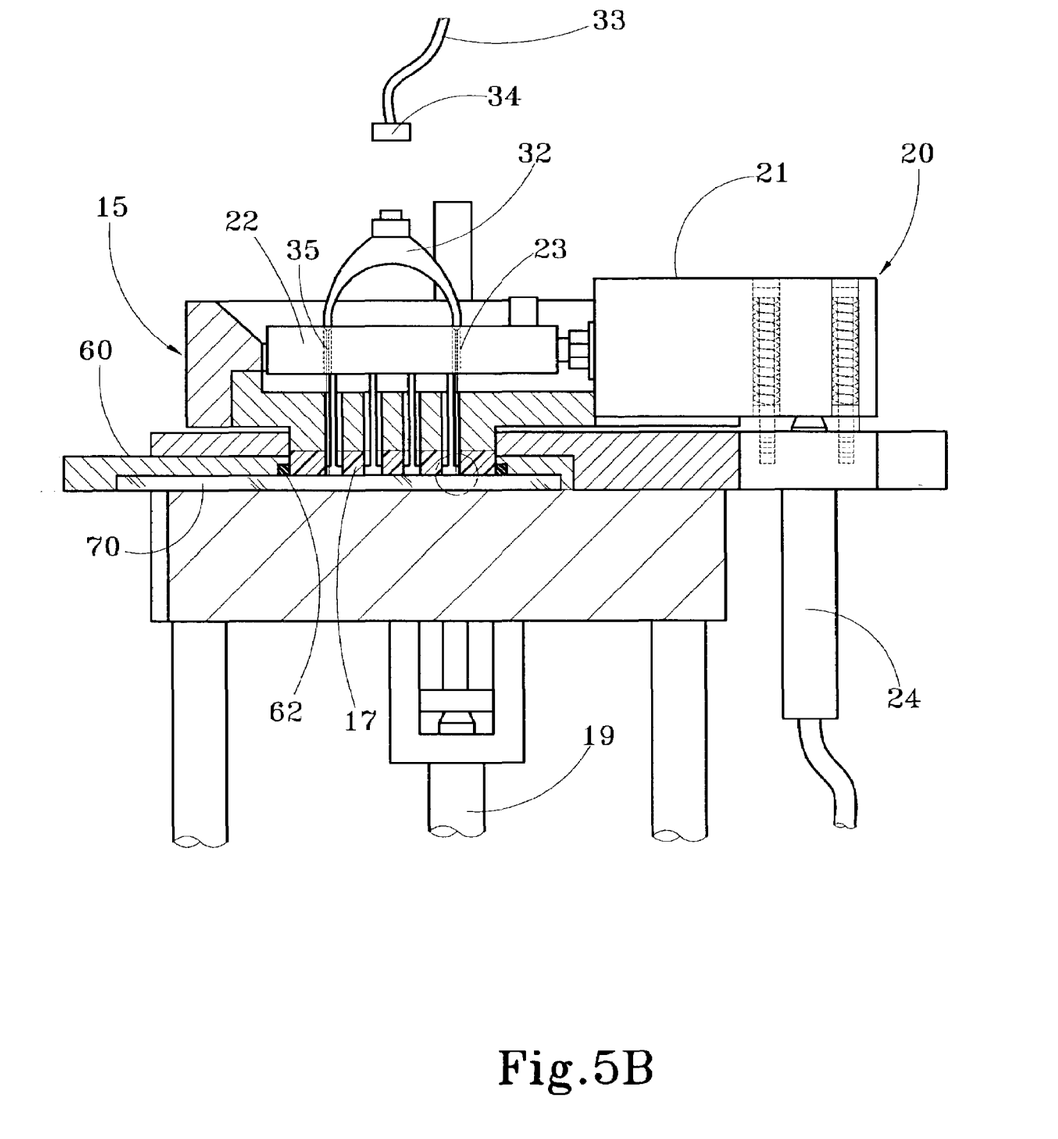
Figure 5C:
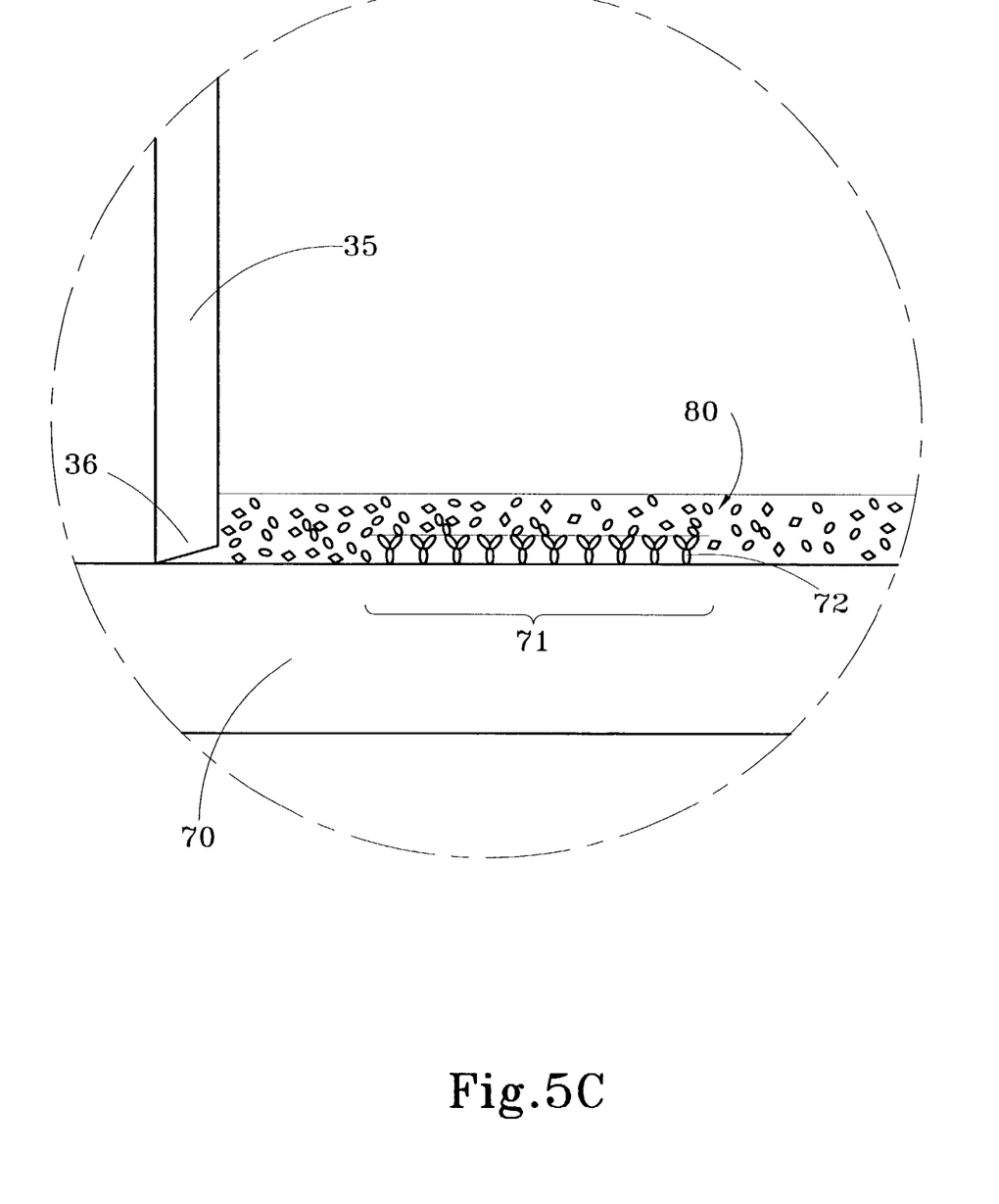

When in use, first adding biological probes 72 on the biochip 70 encased in the chip cartridge 60, or inserting the chip 70 in the positioning device 10, and sequentially adding the biological probes 72 and sample solution 80. The process steps include:

1. first, as shown in FIGS. 4-A and 4-B, insert the biochip 70 through the guiding trough 11 in the positioning device 10; two sides of the clip cartridge 60 are harnessed by the elastic elements 14 and compressed by the compression sections 13 at two sides of the anchoring member 12; the seeping guard 62 around the test opening 61 of the chip cartridge 60 compresses the chip to form a solution mixing zone for all array spots 71; then sample solution 80 may be added to process interaction with all array spots 71;
2. then, as shown in FIGS. 4-B and 4-C, operate the control panel 51 to move the separation unit 15 downwards; the anti-permeation pad 17 is moved to depress the biochip 70, and the apertures 18 of the anti-permeation pad 17 match every array spots 71 to form individual reaction zone; then add respectively different biological probe 72 and the sample solution 80 to each array spots 71;
3. thereafter, as shown in FIGS. 5-A, 5-B and 5-C, operate the control panel 51 to move the mixing device 20 and the suction unit 32 above the biochip 70 for a selected distance; connect the connection head 34 to the oscillation suction unit 32; activate the oscillation unit 21 and perform mixing operations through the mixing unit 22 to accelerate molecular interactions; after the mixing operations completed, operate the control panel 51 to activate the power unit 31 to remove at a selected suction speed the sample solution 80 does not react from the biochip surface; and
4. finally, the surface of the biochip 70 is washed and sucked to dry, and the biochip 70 is removed from the guiding trough 11, and inserted into the reading device 40 through the inlet 41; then optically reflective scanning or transmittant scanning may be performed on the array spots 71 of the biochip 70; through the connection slot 52 on the device body 50, reading data may be transmitted to a computer or to further process qualitative and quantitative analyses for the reaction results.

Figure 6A:
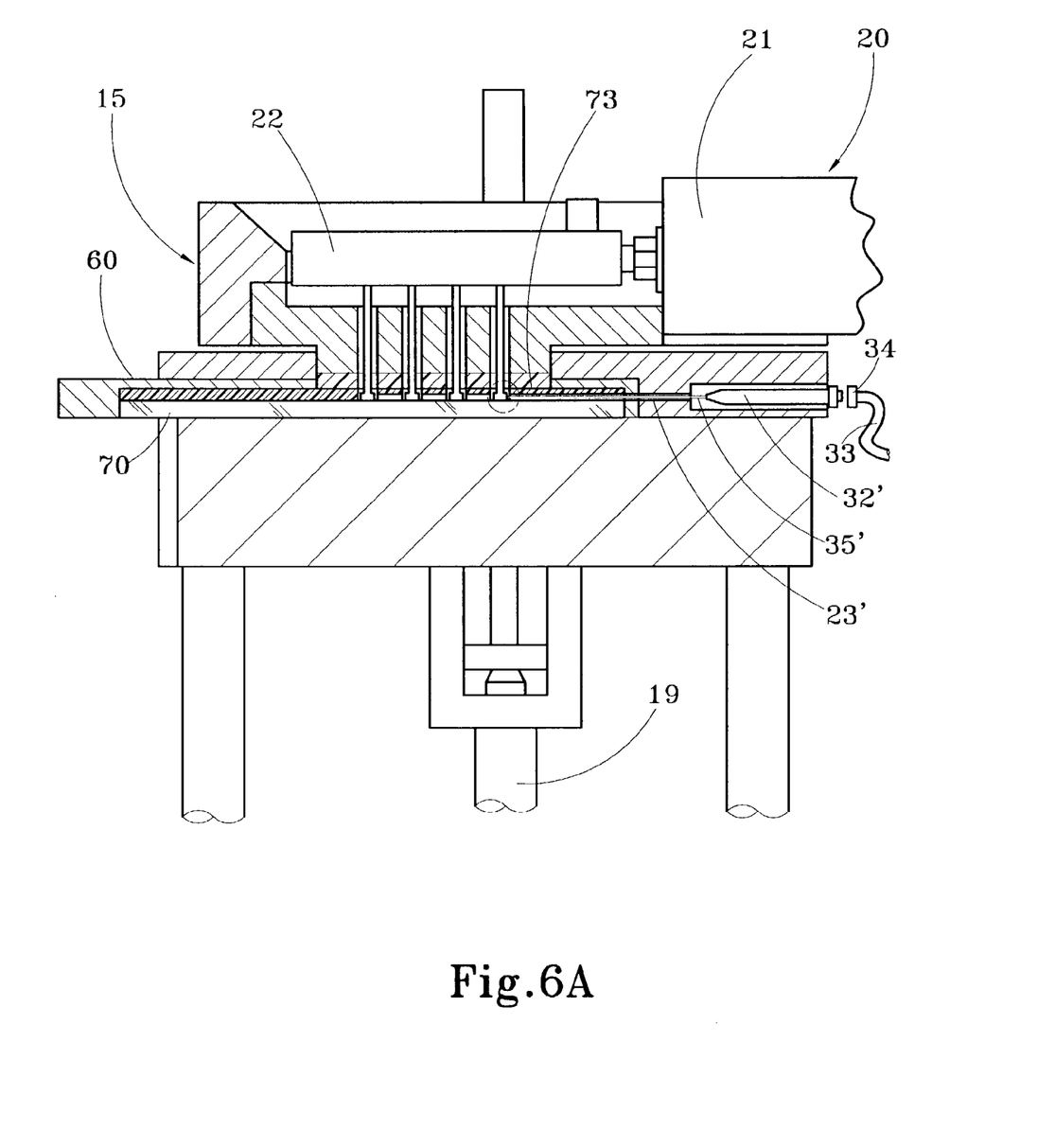
Figure 6B:
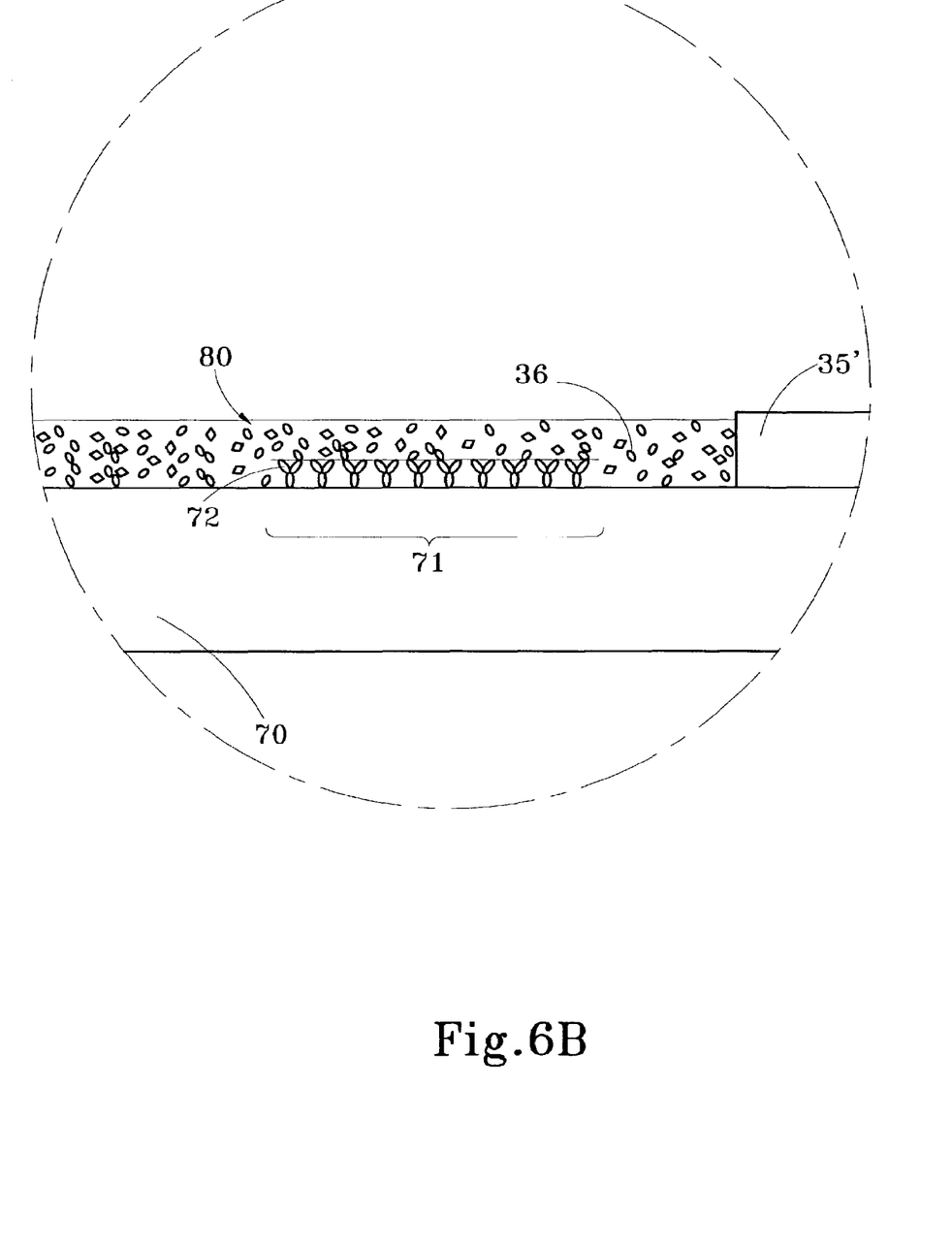

Refer to FIGS. 6-A and 6-B for another embodiment of the invention. In this embodiment, the anchoring hole 23' is located on the rear side of the positioning device 10, and the suction needle 35' of the suction unit 32 is located in the anchoring hole 23' to match operation of another type of biochip 70 which contains a microfluidic chip 73. When to withdraw the sample solution 80 that does not react, the connection head 34 is coupled with the suction unit 32' and the suction needle 35' is horizontally inserted into the microfluidic chip 73 to perform suction operation. Thus form an array biochip workstation that can process a reactive chip and a microfluidic chip.

What is claimed is:

1. An array biochip workstation with at least one biochip, the workstation positions chips, mixes sample solution, and washes and processes qualitative and quantitative testing analyses, comprising:

a positioning device for holding the biochip including a guiding trough for anchoring the biochip and a separation unit located in the guiding trough for separating array spots located on the biochip;

a mixing device located on the positioning device for acting on the sample solution disposed on the biochip having a mixing unit running through the separation unit and corresponding to the array spots to process mixing for the sample solution;

a drawing device for flowing out the sample solution from the biochip surface that fails to react including a power unit and a suction unit fastening to the power unit and adjacent to the array spots on the biochip; and a reading device for detecting reaction results of the biochip and processing qualitative and quantitative scanning analyses for the array spots of the biochip after interaction, washing and flowing out have been completed;

wherein the biochip that has biological probes formed thereon is placed in the positioning device, or the chip is placed in the positioning device, and the biological probes are immobilized thereon, then the sample solution is added, and the mixing device through the separation unit is employed to process mixing on the corresponding array spots of the biochip, and the drawing device is employed to flow out the sample solution that does not react from the biochip surface, then the reading device is used to do analysis and comparison of reaction results for the array spots of the biochip, the guiding trough has two sides forming respectively an anchoring member of a compressing section, the anchoring member being harnessed by an elastic element, a chip cartridge which has two sides clampable by the compressing section holding the biochip, the chip cartridge having a test opening with a periphery coupled with a seeping guard for compressing the biochip to form a common solution mixing zone for all array spots.

2. The array biochip workstation of claim 1, wherein the separation unit has a bottom section attaching to a first displacement mechanism for vertically driving the separation unit in parallel, the separation unit further has a plurality of separation holes corresponding to the array spots of the biochip, the bottom surface of the separation unit further attaching to an anti-permeation pad which has apertures corresponding to the separation holes such that when the separation unit is moved downwards the anti-permeation pad compresses and seals the biochip with the apertures matching respectively the array spots to form reaction zones.

3. The array biochip workstation of claim 2, wherein the mixing device has a bottom section attaching to a second displacement mechanism for moving the mixing device horizontally and up or down, and a oscillation unit consisting of piezoelectric ceramic material to generate oscillation to actuate the mixing unit.

4. The array biochip workstation of claim 2, wherein the anti-permeation pad is made of pliable materials including rubber or other anti-permeation materials.

5. The array biochip workstation of claim 1, wherein the suction unit has at least one suction needle adjacent to the biochip, the suction needle having a head end which forms an obtuse truncated angle, the head end being spaced from the biological probes located on the array spots for a selected distance to prevent reaction results from damaging when the drawing is performed.

6. The array biochip workstation of claim 5, wherein the biochip contains a microfluidic chip, the suction unit being horizontally coupled with the microfluidic chip to process the drawing of solution.

7. The array biochip workstation of claim 1, wherein the reading device is an optical transmittant or reflective scanner depending on the nature of substrates and film property of the biochip.

8. The array biochip workstation of claim 1, wherein the positioning device, the mixing device, the drawing device and the reading device are mounted on a device body, the device body having at least one control panel located on a surface thereof for controlling all other devices and at least one connection slot for linking to a computer or other operation systems to process control and data analysis.

9. The array biochip workstation of claim 8, wherein the device body has at least one housing cavity corresponding to two sides of the positioning device for housing a container for holding the reaction reagents or the sample solution.

* * * * *